(12) United States Patent
Günther

(10) Patent No.: US 8,231,706 B2
(45) Date of Patent: Jul. 31, 2012

(54) METHOD AND DEVICE FOR SEPARATING METHANE AND CARBON DIOXIDE FROM BIOGAS

(75) Inventor: Lothar Günther, Geretsried (DE)

(73) Assignee: MT-Biomethan GmbH, Zeven (DE)

( * ) Notice: Subject to any disclaimer, the term of this patent is extended or adjusted under 35 U.S.C. 154(b) by 564 days.

(21) Appl. No.: 12/442,285

(22) PCT Filed: Mar. 19, 2007

(86) PCT No.: PCT/EP2007/002410
§ 371 (c)(1),
(2), (4) Date: Mar. 20, 2009

(87) PCT Pub. No.: WO2008/034473
PCT Pub. Date: Mar. 27, 2008

(65) Prior Publication Data
US 2010/0024647 A1    Feb. 4, 2010

(30) Foreign Application Priority Data
Sep. 20, 2006  (DE) .................. 10 2006 044 192

(51) Int. Cl.
*B01D 53/14*  (2006.01)
(52) U.S. Cl. .................. 95/11; 95/181; 95/183; 95/211; 95/235; 95/236; 423/228; 423/229
(58) Field of Classification Search .............. 95/183, 95/209, 193–194, 211, 235–236; 423/228–229; 96/234, 242, 290
See application file for complete search history.

(56) References Cited

U.S. PATENT DOCUMENTS

| | | | |
|---|---|---|---|
| 4,409,102 A | | 10/1983 | Tanner |
| 4,496,371 A | * | 1/1985 | Urban et al. .................. 95/174 |
| 4,622,213 A | * | 11/1986 | Urban et al. ............ 423/244.05 |
| 5,597,402 A | * | 1/1997 | LaPack et al. .................. 95/12 |
| 5,871,673 A | * | 2/1999 | Nakagami .................. 252/580 |
| 5,871,674 A | * | 2/1999 | Leva .................. 261/94 |
| 6,569,332 B2 | * | 5/2003 | Ainsworth et al. ........... 210/603 |
| 6,709,592 B2 | * | 3/2004 | van Groenestijn et al. ... 210/603 |
| 7,169,821 B2 | * | 1/2007 | Branson .................. 518/702 |
| 7,666,813 B2 | * | 2/2010 | Hoefer et al. .................. 502/401 |
| 2005/0093183 A1 | * | 5/2005 | Lewis et al. .................. 261/94 |

FOREIGN PATENT DOCUMENTS

DE      20300663 U1    8/2004
DE  102005051952 B3   12/2006

OTHER PUBLICATIONS

Bishnupada Mandal, et al: "Simultaneous Absorption of CO2 and H2S into Aqueous Blends of N-Methyldiethanolamine and Diethanolamine", Environ Science Technology, XP002444694, Aug. 19, 2006, pp. 6076-6084.

* cited by examiner

*Primary Examiner* — Duane Smith
*Assistant Examiner* — Ives Wu
(74) *Attorney, Agent, or Firm* — Laurence A. Greenberg; Werner H. Stemer; Ralph E. Locher

(57) ABSTRACT

A method for separating methane and carbon dioxide from biogas and a device are intended for purifying biogas, wherein carbon dioxide is separated off from the biogas. The method is distinguished by an energetically favorable mode of operation. The biogas is passed under atmospheric pressure and standard temperature into an absorption column. While the biogas ascends through a packed bed, which has a surface area of 600 to 1200 $m^2/m^3$, and at a space velocity of 5 to 40 $Nm^3/m^3h$, carbon dioxide present in the biogas is bound in a wash liquid by chemosorption. The purified methane gas is taken off at the top of the absorption column at a defined flow velocity. Carbon dioxide bound in the wash liquid is removed by desorption at a relatively high pressure of 2 to 30 bar and a temperature of at least 120° C. Biogas may be separated into methane and $CO_2$.

14 Claims, No Drawings

METHOD AND DEVICE FOR SEPARATING METHANE AND CARBON DIOXIDE FROM BIOGAS

BACKGROUND OF THE INVENTION

Field of the Invention

The invention relates to a method of separating methane and carbon dioxide from biogas and to a device for carrying out the method. These are intended for purifying biogas, wherein carbon dioxide is separated off from the biogas.

The known biogases have the following compositions:

| | |
|---|---|
| Methane | 40 to 70% by volume |
| Hydrogen | up to 2% by volume |
| $CO_2$ | up to 60% by volume |
| Nitrogen | up to 5% by volume |
| Oxygen | up to 2% by volume |
| $H_2O$ | 2 to 4% by volume |
| $H_2S$ | 0.01 to 0.6% by volume |

The gas is processed in accordance with the known methods of separating carbon dioxide and purifying refinery gas by pressure washing at a pressure of 10 to 30 bar, using different washing solutions, such as amines, $H_2O$, methanol or acetone, at temperatures between 10 to 40° C. in an absorption column, wherein the proportions of carbon dioxide present in the refinery gas are bound in a washing solution. The washing solution used, which is discharged from the absorption column and is charged with carbon dioxide, is then depressurised to a pressure of 1 to 5 bar and conducted to a desorption column in which the carbon dioxide present in the washing solution is expelled with the application of heat. The carbon dioxide separated off is discharged from the desorption column into the surroundings, or further liquefied by subsequent purifying and compression. Methods are also known for carrying this out. The gas purified by the methods used consists principally of methane and hydrogen, with the content of carbon dioxide having being removed to as little as under 20 ppm.

Dependent on the scrubbing agent used, it is also possible to simultaneously separate off $H_2O$, COS (organic sulphur compounds) or $SO_2$, as well as the carbon dioxide. These components are then present in the carbon dioxide that has been separated off.

It is further known that, in accordance with the same principle, a process gas is purified in the manufacture of ammonia using potash as a scrubbing agent. The separated carbon dioxide is discharged in this process into the surroundings in a gaseous form at a pressure of up to 5 bar.

A method is known (DE 203 00 663 U1) of separating methane and $CO_2$ from biogas in which biogas is mixed in a liquid ring compressor with a wash liquid (polyethylene glycol ether), the gas/liquid mixture is compressed to a pressure of 8 bar and the compressed gas/liquid mixture is fed into an adsorption column with a packed bed of stainless steel bodies in which the polyethylene glycol ether is sprayed as a sealing liquid. Carbon dioxide and hydrogen sulphide are physically bound in the wash liquid in this process. The wash liquid accumulates at the column sump and the compressed methane gas is separated off at the top of the column. The separated wash liquid is depressurised, regeneratively processed and returned to the adsorption column.

Pressures losses occur in a physical pressure washing and high concentrations of biomethane lead to losses of methane gas. In addition, the $CO_2$ is not completely removed. Special safety requirements have to be taken into account in the design and manufacture of the absorption column which lead to increased expenditure and additional costs.

If the biogas, the biomethane, purified under pressure in accordance with the known methods is to be fed into a natural gas network system, it must be depressurised again, since the natural gas network system operates at a considerably lower pressure. This method is inefficient in its use of energy.

The purpose of the invention is to devise a method of separating methane and $CO_2$ from biogas which is distinguished by an energetically favourable mode of operation. In addition, a suitable device for carrying out the procedure is to be devised.

BRIEF SUMMARY OF THE INVENTION

Description of the Invention

The biogas, purified in advance as necessary, is conducted to an absorption column in which the carbon dioxide present in the biogas is removed under atmospheric pressure and standard temperature. The biogas is free of carbon dioxide at the outlet of the absorption column unless a specified residual content of $CO_2$ has been set. It is advantageous for absorption under atmospheric pressure and standard temperature if the packed beds have the largest possible surface area. The packed bed should preferably have a surface area of 600 to 1200 $m^2/m^3$. The space velocity should be 5 to 40 $Nm^3/m^3h$. As the biogas ascends through the packed bed, the carbon dioxide present in the biogas is bound in the wash liquid by chemosorption. The contact time between the wash liquid and the biogas should be preferably 50 to 400 seconds, but not less than at least 40 seconds, in order to ensure that the methane gas produced is of a high degree of purity.

The respective contact time depends on the carbon dioxide concentration in the biogas and the amine concentration in the washing solution. The temperature of the biogas and the washing solution in the main have no effect here in the range of 10 to 50° C.

The contact time is set by a controlled biomethane extraction from the gas scrubber via a compressor, according to the desired scrubbed gas value for $CO_2$ which is measured.

Biogas may be separated particularly economically into methane and $CO_2$ by the suggested procedure. No methane losses occur and the $CO_2$ can be completely separated, apart from marginal amounts in the ppm region. The energy expenditure for any compression of the methane gas required is 50% less than with pressure washing, since the $CO_2$ has already been almost completely separated and the amount of gas to be compressed is therefore considerably less.

The flow velocity of the biogas is set on intake into the absorption column at 0.01 to 0.1 m/s based on the available cross-section of the column.

An amine solution, consisting of diethanolamine for example dissolved in water at a concentration of 20% by weight, should preferably be used as a wash liquid. The washing solution used is at approximately the same temperature as the biogas fed in. The advantage of this is that the water balance in the scrubbing column can be kept constant which also ensures that the amine concentration does not change.

After absorption in the wash liquid, the carbon dioxide that is still bound is then removed by means of desorption at a relatively high pressure of 2 to 30 bar and at a temperature of at least 120° C. Steam or thermal oil can be used as the heat exchanger medium for desorption.

An effective way of producing methane gas of a higher purity, for example 99.5%, is to purify the biogas before it is fed into the absorption column by means of a suitable scrubbing and/or adsorption process in order to remove the proportions of $NH_3$, COS (organic sulphur compounds), $H_2S$ and $SO_2$ present in the biogas.

The biomethane removed from the absorption column at atmospheric pressure can be conducted over a drying unit or a police filter and then fed either into a natural gas network system or utilised in some other way.

Compressors made of mild steel can be used for compressing the biomethane where that is necessary. A device suitable for carrying out the method should be designed in such a way that the necessary installed components in the absorption column, the packed bed, have a surface area of 600 to 1200 $m^2/m^3$ and a space velocity factor of 5 to 40 $Nm^3/m^3h$, preferably 20 $Nm^3/m^3h$. The individual packed beds should have an average diameter of 5 to 8 mm. A space velocity or a space velocity factor of 5 to 40 $Nm^3/m^3h$ means that a reaction volume of at least 1 $m^3$ is required for an amount of biogas fed into the absorption column at 5 to 40 $Nm^3/h$. The reaction volume is determined by the packed beds used which have an extremely large surface area compared with their size. Small packed beds like these which produce a large contact surface area are completely unsuitable for use in pressure washing. Based on the required large surface area of the packed bed (600 to 1200 $m^2/m^3$), the extraction or flow velocity of the methane and the dwell or contact times of the biogas in the gas scrubber from 50 to 400 seconds for example, can be set by a controlled extraction of methane in order to guarantee an almost complete removal of the $CO_2$. If necessary, a desired residual content of $CO_2$ in the methane gas can also be set.

Dependent on the amount of biogas to be purified and the required reaction volume of the packed bed, the absorption column constructed as a cylindrical vessel should have a length/diameter ratio of 4 to 20, preferably 10 to 20 or 14 to 18. It is also advantageous if the column can be made smaller in height than a pressure scrubber. The length/diameter ratio of the absorption column depends essentially on the amount of biogas to be processed.

The basic structure of the absorption column suggested for the removal of $CO_2$ equates to that of a gas scrubber. Because of the special design of the packed bed, the process control of the biogas within the column for removing $CO_2$ by chemosorption equates to the mode of operation of a reactor.

The washing solution discharging from the absorption column at a temperature of 10 to 50° C. is compressed to a pressure of 2 to 30 bar, heated by conventional regeneration by heat input to a temperature of 120 to 180° C., preferably up to 160° C. and conducted to a desorption column/flash depressurisation unit where the carbon dioxide and steam are separated. The purified washing solution is conducted back to the scrubbing column, which is at atmospheric pressure.

Producing biomethane at atmospheric pressure, a process which saves about 50% of compressor capacity enables inexpensive materials to be used. This is not possible with pressure scrubbing or with another method of pressure cleaning.

The invention is explained below by means of two examples.

EXAMPLE 1

An absorption or scrubbing column with a length of 12 m and a diameter of 1.75 m is used for separating methane and $CO_2$ from biogas. A packed bed is positioned as a built-in component consisting of packed beds with an average diameter of 5 to 8 mm and a specific surface of 800 $m^2/m^3$. The packed beds are made of plastic, preferably polypropylene.

The packed bed positioned above the sump has a column bed height of 8 m. The column volume of the packed bed is therefore 19.23 $m^3$. Based on the design of the column with a length/diameter ratio of 4:57, the biogas to be purified assumes a flow velocity of 0.062 m/s based on the available column cross-section on feeding in 500 Nm3/h of biogas at the column intake (N=atmospheric pressure and standard temperature).

This gives a space velocity factor of 26.3 under the above-named conditions.

Biogas at a temperature of 25° C. and a pressure of 1015 mbar is fed into the column below its base at a rate of 500 $Nm^3/h$. The pre-purified biogas which is fed in has the following composition:

| | |
|---|---|
| $CH_4$ | 53.5% by volume |
| $CO_2$ | 44.0% by volume |
| $H_2O$ | 2.5% by volume |
| $H_2S$ | 150 ppm |

An amine-containing washing solution consisting of water and diethanolamine at a concentration of 20% by weight and at a temperature of 25° C. is sprayed in at the top of the scrubbing column as a scrubbing agent at a rate of 15 $m^3/h$.

The washing solution is circulated in the circuit and re-used, after regeneration, especially the separation of the residues of $CO_2$ and $H_2S$, has taken place.

The biogas fed in at atmospheric pressure flows through the packed bed in the counter flow process, thereby coming into contact with the washing solution. The contact time until the $CO_2$ and sulphur compounds present in the biogas are almost completely separated off is 138 seconds. The $CO_2$ and sulphur compounds are chemically bound in the washing solution in this process.

The methane gas formed at the top of the scrubbing column is separated off by means of a downstream compressor. At the same time, the $CO_2$ concentration in the methane gas is measured, and the rotational speed of the compressor is regulated according to the measured value. The contact time within the scrubbing column is set by the rotational speed of the compressor. The methane separated off at the column outlet is extracted at a flow velocity of 0.033 m/s and has the following composition:

| | |
|---|---|
| $CH_4$ | 97.3% by volume |
| $CO_2$ | 0.2 by volume |
| $H_2O$ | 2.5% by volume |
| $H_2S$ | 1 ppm |

EXAMPLE 2

An absorption or scrubbing column is used with a length of 12 m and a diameter of 0.45 m for separating methane and $CO_2$ from biogas. A packed bed is positioned as a built-in component composed of packed beds with an average diameter of 5 to 8 mm and a fixed surface area of 800 $m^2/m^3$. The packed beds are made of plastic, preferably polypropylene.

The packed bed positioned above the sump has a column bed height of 8 m. The column volume of the packed bed is therefore 1.27 $m^3$. Based on the design of the column with a length/diameter ratio of 17:8, the biogas to be purified assumes a flow velocity of 0.043 m/s based on the available column cross-section on feeding in 25 Nm³/h of biogas at the column intake (N=standard temperature and pressure). This gives a space velocity factor of 19.7 under the above-named conditions.

Biogas at a temperature of 28° C. and a pressure of 1015 mbar is fed into the column below its base at a rate of 25 Nm³/h. The biogas fed in has the following composition:

| | |
|---|---|
| $CH_4$ | 51.1% by volume |
| $CO_2$ | 46.0% by volume |
| $H_2O$ | 2.9% by volume |
| $H_2S$ | 80 ppm |

An amine-containing washing solution consisting of water and diethanolamine at a concentration of 30% by weight and at a temperature of 15° C. is sprayed in at the top of the scrubbing column as a scrubbing agent at a rate of 45 m³/h.

The washing solution is circulated in the circuit and after regeneration, especially the separation of the residues of $CO_2$ and $H_2S$, is re-used.

The biogas fed in at atmospheric pressure flows through the packed bed in the counter flow process, thereby coming into contact with the washing solution. The $CO_2$ and sulphur compounds present in the biogas are almost completely removed and bound in the washing solution in this process. The methane gas formed at the top of the scrubbing column is separated off by a downstream compressor. At the same time, the $CO_2$ concentration in the methane gas is measured, and the rotational speed of the compressor is regulated according to the measured value. The contact time within the scrubbing column is set via the rotational speed of the compressor. In this example a contact time of 184 seconds is set for completely removing the $CO_2$ by the compressor. The methane separated off at the column outlet is extracted at a flow velocity of 0.025 m/s and has the following composition:

| | |
|---|---|
| $CH_4$ | 98.4% by volume |
| $CO_2$ | 0.1 by volume |
| $H_2O$ | 1.5% by volume |
| $H_2S$ | 0.1 ppm |

Extremely pure methane with the following composition is obtained by dehumidifying the methane to a residual water content of 50 mg/Nm³:

| | |
|---|---|
| $CH_4$ | 99.80% by volume |
| $CO_2$ | 0.12 by volume |
| $H_2O$ | 50 mg/Nm³ |
| $H_2S$ | 0.1 ppm |

There is only 0.08% by volume of hydrogen and $CO_2$ left in the dehumidified methane. The methane gas can therefore be fed into a local natural gas network system immediately without further processing or utilised in some other way.

The invention claimed is:

1. A method of separating methane and carbon dioxide from biogas, which comprises the steps of:
    scrubbing in an absorption column in which the biogas ascends through a packed bed in counter flow to a wash liquid which is fed in and binds the carbon dioxide and hydrogen sulphide, and for subsequent regeneration of the wash liquid;
    conducting the biogas into the absorption column under atmospheric pressure and standard temperature, wherein the carbon dioxide present in the biogas is bound in the wash liquid by chemosorption as the biogas ascends through the packed bed;
    separating off the methane gas at a top of the absorption column at a defined flow velocity;
    subsequently removing the carbon dioxide still bound in the wash liquid by desorption at a relatively high pressure of 2 to 30 bar and a temperature of at least 120° C.; and
    measuring a $CO_2$ concentration in the methane gas and a flow velocity of the removed methane gas, and thus the contact time, is set according to a value measured.

2. The method according to claim 1, which further comprises flowing the biogas in the absorption column through the packed bed having a surface area of 600 to 1200 m²/m³ and a space velocity of 5 up to 40 Nm³/m³h.

3. The method according to claim 1, which further comprises setting a flow velocity of the biogas based on an available column cross-section at 0.01 to 0.1 m/s.

4. The method according to claim 1, which further comprises providing an amine solution as the wash liquid.

5. The method according to claim 4, which further comprises adjusting a contact time of the scrubbing in response to an amine concentration of the wash liquid.

6. The method according to claim 1, which further comprises keeping a water balance of the wash liquid constant by setting a biogas temperature and a temperature of the wash liquid circulated in a circuit.

7. The method according to claim 1, wherein the desorption takes place at a pressure of 8 to 20 bar.

8. The method according to claim 1, wherein the desorption takes place at temperatures of up to 180° C.

9. The method according to claim 1, which further comprises using one of steam and thermal oil as a heat exchanger medium for the desorption.

10. The method according to claim 1, which further comprises removing proportions of $NH_3$, COS, $H_2S$ and $SO_2$ present in the biogas before the biogas is fed into the absorption column.

11. The method according to claim 1, further comprising the step of setting a contact time of the scrubbing to be at least 40 seconds.

12. The method according to claim 1, which further comprises adjusting a contact time of the scrubbing in response to an amine concentration of the wash liquid.

13. The method according to claim 11, which further comprises feeding in the biogas and the wash liquid at a same temperature.

14. The method according to claim 11, which further comprises setting the contact time for scrubbing from 50 to 400 seconds.

* * * * *